(12) United States Patent
Takakura et al.

(10) Patent No.: US 9,573,982 B2
(45) Date of Patent: Feb. 21, 2017

(54) MODIFIED TAMAVIDIN

(75) Inventors: Yoshimitsu Takakura, Oyama (JP); Naomi Oka, Iwata (JP)

(73) Assignee: JAPAN TOBACCO INC., Tokyo (JP)

( * ) Notice: Subject to any disclaimer, the term of this patent is extended or adjusted under 35 U.S.C. 154(b) by 83 days.

(21) Appl. No.: 13/885,655

(22) PCT Filed: Dec. 28, 2011

(86) PCT No.: PCT/JP2011/080451
§ 371 (c)(1),
(2), (4) Date: May 15, 2013

(87) PCT Pub. No.: WO2012/091110
PCT Pub. Date: Jul. 5, 2012

(65) Prior Publication Data
US 2013/0309765 A1    Nov. 21, 2013

(30) Foreign Application Priority Data

Dec. 28, 2010 (JP) ................. 2010-293776

(51) Int. Cl.
| | |
|---|---|
| C07H 21/04 | (2006.01) |
| C07K 1/00 | (2006.01) |
| C07K 14/00 | (2006.01) |
| A23J 1/18 | (2006.01) |
| A23J 1/00 | (2006.01) |
| C12N 15/00 | (2006.01) |
| C07K 14/37 | (2006.01) |
| C07K 14/375 | (2006.01) |
| G01N 33/53 | (2006.01) |
| C07K 14/465 | (2006.01) |

(52) U.S. Cl.
CPC ............. *C07K 14/37* (2013.01); *C07K 14/375* (2013.01); *C07K 14/465* (2013.01); *G01N 33/53* (2013.01)

(58) Field of Classification Search
CPC ....... G01N 33/53; C07K 14/465; C07K 14/37; C07K 14/375
USPC ...................................... 536/23.2
See application file for complete search history.

(56) References Cited

FOREIGN PATENT DOCUMENTS

| | | |
|---|---|---|
| EP | 1 369 476 A1 | 12/2003 |
| EP | 2 112 168 A1 | 10/2009 |
| EP | 2 314 681 A1 | 4/2011 |
| JP | WO 2008/081938 A1 * | 7/2008 |
| WO | WO 02/072817 A1 | 9/2002 |
| WO | WO 2010/018859 A1 | 2/2010 |

OTHER PUBLICATIONS

Takakura et al., 2009 FEBS J. 276:1383-1397.*
Nordlund et al 2003, J. Biol. Chem 278:2479-2483.*
Laitinen et al 2007, Trends in Biotechnology 25:269-277.*
Hytonen et al., "Design and Construction of Highly Stable, Protease-resistant Chimeric Avidins," *J. Biol. Chem*. (Mar. 18, 2005), vol. 280, No. 1, pp. 10228-10233.
International Search Report issued Feb. 7, 2012, in PCT International Application No. PCT/JP2011/080451.
Nordlund et al., "Enhancing the Thermal Stability of Avidin," *J. Biol. Chem*. (Jan. 24, 2003), vol. 278, No. 4, pp. 2479-2483.
Reznik et al., "Streptavidins with intersubunit crosslinks have enhanced stability," *Nature Biotechnology* (Aug. 1996) vol. 14, pp. 1007-1011.
Takakura et al. "Tamavidins—novel avidin-like biotin-binding proteins from the Tamogitake mushroom," *FEBS Journal* (2009), vol. 276, pp. 1383-1397.
Extended European Search Report, dated Apr. 23, 2014, for European Application No. 11853702.6.

* cited by examiner

*Primary Examiner* — Kelaginamane T Hiriyanna
(74) *Attorney, Agent, or Firm* — Birch, Stewart, Kolasch & Birch, LLP

(57) ABSTRACT

The present invention provides modified tamabidin 2, which is a modified biotin-binding protein comprising an amino acid sequence represented by SEQ ID NO: 2, an amino acid sequence having one or more amino acid mutations in the amino acid sequence of SEQ ID NO: 2, or an amino acid sequence having an identity of not less than 80% to the amino acid sequence of SEQ ID NO: 2 and having biotin-binding activity, wherein an asparagine residue at position 115 of SEQ ID NO: 2 is replaced with cysteine. The modified biotin-binding protein has remarkable heat resistance.

10 Claims, 3 Drawing Sheets

MODIFIED TAMAVIDIN

TECHNICAL FIELD

This application claims priority of Japanese Patent Application No. 2010-293776 filed on Dec. 28, 2010.

The present invention relates to a modified tamavidin having increased heat resistance.

BACKGROUND ART

Avidin is a basic glycoprotein derived from egg white and strongly binds to biotin (vitamin H). Streptavidin is an avidin-like protein derived from Actinomycetes (*Streptomyces avidinii*) and has a near-neutral isoelectric point and does not have a sugar chain. Both proteins form tetramers, and the molecular weights thereof are about 60 kDa. The tetramer is formed by weak bonds between dimers, while the dimers are composed of strongly bonded monomers. Avidin and streptavidin have the property that one monomer thereof binds to one biotin molecule. Avidin and streptavidin each have significantly high affinity (Kd=$10^{-15}$ to $10^{-14}$ M) to biotin, and the affinity is one of the most strong interactions between two biomolecules. Accordingly, avidin/streptavidin-biotin interaction has been widely used in the fields of biochemistry, molecular biology, and medicine.

Biotin has a small molecular weight of 244 and is stable to a change in pH and heat and, therefore, is commonly used for labeling substances. In a method of biotinylation, chemically modified biotin is bound to a functional group of a target compound. Such biotinylating reagents are commercially available and can be used to biotinylate compounds such as protein and nucleic acid. In one of the methods of biotinylation of proteins, a fusion protein of a target protein and a sequence that can be biotinylated by biotin ligase in a living body is expressed as a recombinant protein, and the resulting fusion protein can be biotinylated by the biotin ligase in a host cell.

The present inventors have discovered tamavidin 1 and tamavidin 2, which are novel avidin-like biotin-binding proteins, in an edible mushroom, *Pueurotus cornucopiae* (WO02/072817). Tamavidin 1 and tamavidin 2 can be expressed in a large amount in *Escherichia coli*. In particular, tamavidin 2 can be easily prepared by purification using an iminobiotin column (WO02/072817). Tamavidin 1 and tamavidin 2 form tetramers and form an extremely strong binding with biotin. Furthermore, tamavidin 2 is an excellent biotin-binding protein in that the protein exhibit a heat resistance higher than that of avidin or streptavidin and that the non-specific binding is less than that of avidin.

Avidin, streptavidin, and tamavidin have higher heat resistance than normal protein and have heat resistance determined by a method using fluorescent biotin (expressed by a temperatures at which their activity decreases to one half the initial activity) of 79° C., 74° C., and 85° C., respectively (Takakura et al. 2009 FEBS J 276: 1383-1397).

For expanding industrial applications, however, attempts to further enhance the heat resistance of avidin and streptavidin have been being made. Reznik et al., (1996) reported streptavidin (Nat. Biotechnol., 14: 1007-1011). Aiming to strengthen the weak bond between the dimers of streptavidin, they mutate a hystidine (His) residue at position 127 into cysteine (Cys) through genetic engineering to construct a heat-resistant disulfide-linked dimer of streptavidin mutants. The mutant maintained about 70% of the original biotin-binding activity after a heat treatment at 90° C. for 10 min, while wild-type streptavidin maintained about 55% of the original biotin-binding activity after a heat treatment at 70° C. for 10 min.

Meanwhile, Nordlund et al. 2003 (J. Biol. Chem. 278: 2479-2483) reported heat stabilization of avidin; they have genetically engineered various forms of disulfide bonds between avidin subunits to increase heat resistance. The residual biotin-binding activity of avidin was almost zero after a treatment at 99.9° C. for 2 min, while the activity of I117C (modified avidin in which isoleucine at position 117 in avidin is replaced with cysteine) was a little more than 30%, and the activity of D86CI106CI117C (modified avidin in which aspartic acid residue at position 86 and isoleucine residues at positions 106 and 117 in avidin are replaced with cysteine residues, respectively) was a little less than 50%.

Furthermore, Hytonen et al., (2005), J. Biol. Chem., 280: 10228-10233 reported heat stabilization of avidin without the formation of disulfide bonding. A chimera of avidin and AVR4 (protein encoded by Avidin-related gene 4) having higher heat resistance than avidin was formed to create an avidin mutant ChiAVD (I117Y), which exhibited increased residual biotin-binding activity of up to 98% after a treatment at 99.9° C. for 32 min (residual activity: 4% for avidin, 72% for AVR4).

Almost all of the heat-resistant avidin mutants are prepared using an insect cell expression system using baculovirusm, while streptavidin mutants are prepared using an *E. coli* expression system, which requires a step of solubilization from insoluble inclusion bodies during the process. Thus, such proteins as described above, any of which require considerable costs and efforts for manufacturing them, have not yet been put into practical application.

CITATION LIST

Patent Literature

Patent Literature 1: International Publication No. WO02/072817

Patent Literature 2: International Publication No. WO2010/018859

Non-Patent Literature

Non-Patent Literature 1: Takakura, et al., (2009), FEBS J., 276: 1383-1397

Non-Patent Literature 2: Reznik et al., (1996), Nat. Biotechnol., 14: 1007-1011

Non-Patent Literature 3: Nordlund et al., (2003), J. Biol. Chem., 278: 2479-2483

Non-Patent Literature 4: Hytonen et al., (2005), J. Biol. Chem., 280: 10228-10233

SUMMARY OF INVENTION

Technical Problem

The problem to be solved by the present invention is to provide a modified tamavidin 2 which can be expressed highly in a soluble form in *E. coli* and has increased heat resistance which can maintain its protein structure even after being heated at a high temperature.

Solution to Problem

The present inventors, who have diligently studied in order to solve the foregoing problems, have successfully obtained a modified tamavidin 2 which is highly expressed in a soluble form in *E. coli* and has increased heat resistance which can maintain its protein structure even after being heated at a high temperature and have arrived at the present invention.

Specifically, in the present invention, a modified biotin-binding protein, which has increased heat resistance strong enough to maintain the biotin-binding activity after a treatment at 99.9° C. for 32 min, is obtained by replacing the 115th asparagine residue in the amino acid sequence (SEQ ID NO: 2) of native tamavidin 2 (hereinafter may be referred to as "TM2" in this specification) with cysteine (SEQ ID NO: 4) This modified tamavidin 2 had also improved resistance to aprotic polar organic solvent.

Preferred Embodiments of Present Invention

The present invention includes the following preferred embodiments.

[Embodiment 1]

A modified biotin-binding protein comprising an amino acid sequence represented by SEQ ID NO: 2, an amino acid sequence having one or more amino acid mutations in the amino acid sequence of SEQ ID NO: 2, or an amino acid sequence having an identity of not less than 80% to the amino acid sequence of SEQ ID NO: 2 and having biotin-binding activity, wherein an asparagine residue at position 115 of SEQ ID NO: 2 is replaced with cysteine.

[Embodiment 2]

The modified biotin-binding protein according to embodiment 1, wherein the modified biotin-binding protein maintains the biotin-binding activity of not less than 75% after a heat treatment of 99.9° C. for 30 min, compared with that of before the treatment.

[Embodiment 3]

The modified biotin-binding protein according to embodiment 1 or embodiment 2, wherein the modified biotin-binding protein maintains not less than 50% of the biotin-binding activity of not less than 50% after a treatment in 60% aprotic polar organic solvent for 30 min, compared with that of before the treatment.

[Embodiment 4]

The modified biotin-binding protein according to embodiment 3, wherein the aprotic polar organic solvent is dimethyl sulfoxide.

[Embodiment 5]

The modified biotin-binding protein according to any one of embodiments 1 to 4, wherein the modified biotin-binding protein comprises an amino acid having an identity of not less than 90% to the amino acid sequence of SEQ ID NO: 2.

[Embodiment 6]

The modified biotin-binding protein, wherein an asparagine residue at position 115 of SEQ ID NO: 2 is replaced with cysteine (TM2 N115C). [Embodiment 7]

A support to which the protein according to any one of embodiments 1 to 6 is immobilized.

[Embodiment 8]

A nucleic acid encoding the protein according to any one of embodiments 1 to 6.

[Embodiment 9]

A vector containing the nucleic acid according to embodiment 8.

[Embodiment 10]

A method for separation, concentration, capture, purification, and/or detection of the protein according to any one of embodiments 1 to 6, which comprises the following steps:
1) heat-treating a sample containing the protein at a temperature of at least 90° C. for at least 10 min; and 2) collecting the protein which has not been heat-denatured in step 1) to thereby separate, concentrate, capture, or purify the protein, and/or detect the protein.

[Embodiment 11]

A method for separation, concentration, capture, purification and/or detection of a biotin-linked substance, which comprises the following steps:
1) contacting the support according to mode 7 with a biotin-linked substance, whereby the biotin-linked substance is bound to the support;
2) washing off contaminants which are not bound to the support with a solution containing 60% to 80% aprotic polar organic solvent; and
3) collecting the biotin-linked substance which is bound to the support to thereby separate, concentrate, capture or purify the substance and/or detect the substance.

[Embodiment 12]

The method according to embodiment 11, wherein the aprotic polar organic solvent is dimethyl sulfoxide.

ADVANTAGEOUS EFFECTS OF INVENTION

The present invention provides modified TM2 that can be highly expressed in *E. coli* in a soluble form and exhibits enhanced heat resistance which can maintain its protein structure even after being heated at a high temperature. The modified TM2 of the present invention, which has high heat resistance, can be purified by, for example, thermal purification. The modified TM2 also exhibits enhanced resistance to aprotic polar organic solvent. The modified TM2 of the present invention having resistance to organic solvent can be washed with a solvent such as dimethyl sulfoxide to suppress non-specific adsorption during the separation and purification of biotin-linked substances. Furthermore, the modified TM2 of the present invention can also be used, for example, in systems for immobilizing or detecting substances in organic solvents.

DESCRIPTION OF EMBODIMENTS

Figure 1:
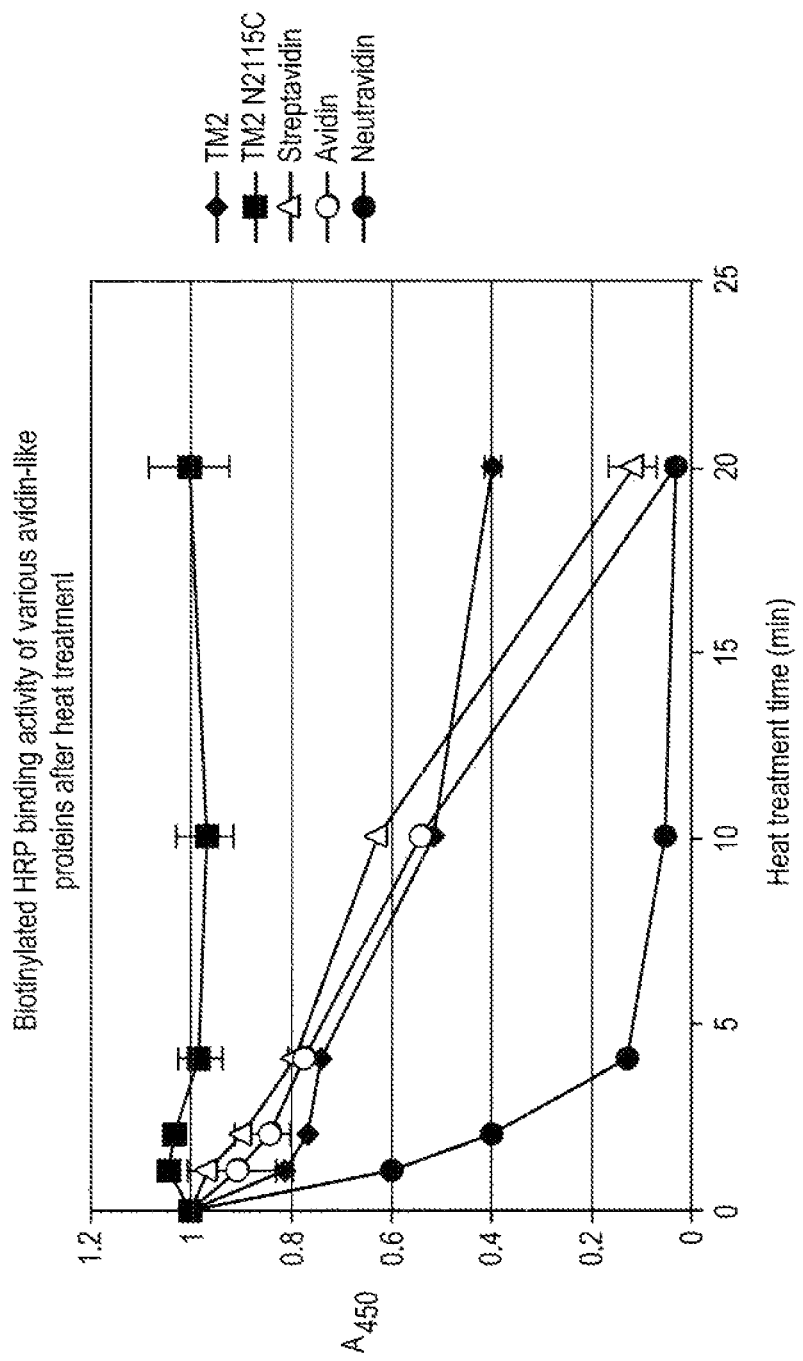
FIG. 1 is a graph showing the biotin-binding ability after heat treatment of the modified TM2 N115C of the present invention, TM2, and various avidin-like proteins (streptavidin, avidin, and neutravidin). The heat treatment was carried out at 99.9° C. for 1, 2, 4, 10 and 20 min.

Preferred embodiments for implementing the present invention will be described below.

Tamavidin

Tamavidin is a novel biotin-binding protein discovered in an edible mushroom, Basidiomycete, *Pleurotus cornucopiae* (WO02/072817). This reference states that:

tamavidin 1 and tamavidin 2 have an amino acid homology of 65.5% and strongly bind to biotin;

tamavidin 2 is highly expressed in a soluble fraction of *E. coli*; and culture of *E. coli* for expressing tamavidin 2 for 4.5 hours gives about 1 mg of a highly pure recombinant protein for 50 mL of a culture medium. This is a significantly high value compared to those of avidin and streptavidin known as biotin-binding proteins.

Throughout the specification, the term "tamavidin 2" refers to tamavidin 2 (TM2) or a mutant thereof. The present invention provides modified TM2 that has enhanced heat resistance by modifying a specific amino acid residue of TM2 or a mutant thereof. Throughout the specification, "tamavidin 2" and "TM2" refer to wild-type TM2 and mutants thereof, unless specifically mentioned. However, depending on the context, they may be used as general terms of wild-type TM2, its mutants, and modified TM2 of the present invention. In addition, TM2, which shows biotin-binding affinity, may be referred to as "biotin-binding protein" throughout the specification.

Specifically, TM2 (wild-type) may be typically a protein comprising the amino acid sequence represented by SEQ ID NO: 2 or a protein encoded by a nucleic acid including the nucleotide sequence represented by SEQ ID NO: 1. Alternatively, TM2 may be a protein that is a mutant of the protein comprising the amino acid sequence represented by SEQ ID NO: 2 or of the protein encoded by the nucleic acid comprising the nucleotide sequence represented by SEQ ID NO: 1 and has biotin-binding activity similar to that of tamavidin 2. The mutant of TM2 may be a protein comprising an amino acid sequence having deletion, substitution, insertion, and/or addition of one or more amino acids in the amino acid sequence of SEQ ID NO: 2. The substitution may be conservative substitution. The conservative substitution refers to the replacement of a specific amino acid residue with any residue having similar physicochemical characteristics. Nonlimiting examples of the conservative substitution include substitution between amino acid residues containing aliphatic groups, such as mutual substitution among Ile, Val, Leu, and Ala, and substitution between polar residues, such as mutual substitution between Lys and Arg, between Glu and Asp, and between Gln and Asn.

The mutant by deletion, substitution, insertion, and/or addition of an amino acid or amino acids can be prepared by a known technique such as site-directed mutagenesis (e.g., see Nucleic Acid Research, Vol. 10, No. 20, pp. 6487-6500, 1982, the entity thereof is incorporated therein by reference) to a DNA encoding a wild-type protein. Throughout the specification, the term "one or more amino acids" refers to an amino acid or amino acids that may be deleted, substituted, inserted, and/or added by site-directed mutagenesis. In addition, the term "one or more amino acids" in this specification may refer to one or several amino acids in some cases.

TM2 of the present invention includes, but not limited to, a protein composed of an amino acid sequence having deletion, substitution, insertion, and/or addition of 1 to 10 amino acids, preferably 9 or less, 7 or less, 5 or less, 3 or less, 2 or less, more preferably one amino acid or less in SEQ ID NO: 2 and having biotin-binding activity.

In the present invention, for example, tamavidin with high binding and low nonspecific binding ability (WO2010/018859) can be used without limitation as a TM2 mutant. Examples of the tamavidin 2 mutant may be; a biotin-binding protein comprising an amino acid sequence represented by SEQ ID NO: 2, an amino acid sequence having one to several amino acid mutations in the sequence represented by SEQ ID NO: 2, or an amino acid sequence having an identity of not less than 80% to the sequence represented by SEQ ID NO: 2, and having a biotin-binding activity, wherein one or more residue(s) selected from the group consisting of:

1) an arginine residue at position 104 of SEQ ID NO: 2;
2) a lysine residue at position 141 of SEQ ID NO: 2;
3) a lysine residue at position 26 of SEQ ID NO: 2; and
4) a lysine residue at position 73 of SEQ ID NO: 2 is replaced with an acidic amino acid residue or a neutral amino acid residue.

More preferably, the biotin-binding protein may be selected from the group consisting of:

a biotin-binding protein (R104E-K141E) in which the arginine residue at position 104 of SEQ ID NO: 2 is replaced with glutamic acid residue, and a lysine residue at position 141 is replaced with a glutamic acid residue;

a biotin-binding protein (D40N-R104E) in which the aspartic acid residue at position 40 of SEQ ID NO: 2 is replaced with asparagine residue, and an arginine residue at position 104 is replaced with a glutamic acid residue;

a biotin-binding protein (D40N-K141E) in which the aspartic acid residue at position 40 of SEQ ID NO: 2 is replaced with asparagine residue, and the lysine residue at position 141 is replaced with glutamic acid residue; and a biotin-binding protein (D40N-R104E-K141E) in which the aspartic acid residue at position 40 of SEQ ID NO: 2 is replaced with asparagine residue, the arginine residue at position 104 is replaced with glutamic acid residue, and the lysine residue at position 141 is replaced with glutamic acid residue.

The site-directed mutagenesis can be performed, for example, with a synthetic oligonucleotide primer that is complementary to a single-strand phage DNA to be mutated, except for a specific mismatch, i.e., a desired mutation. Specifically, the synthetic oligonucleotide is used as a primer to synthesize a strand complementary to the phage, and a host cell is transformed with the resulting double-strand DNA. The transformed bacterial culture is plated on agar to form plaques from phage-containing single cells. As a result, in theory, 50% of the new colonies contain phages having the mutation in a single strand, while the remaining 50% have the original sequence. The resulting plaques are hybridized with a synthetic probe labeled by kinase treatment at a temperature that allows for hybridization with DNA completely identical to one having the above desired mutation, but not with DNA having the original strand. Subsequently, the plaques hybridized with the probe are picked and cultured to collect the DNA.

Examples of the method of introducing deletion, substitution, insertion and/or addition of one or more amino acids in the amino acid sequence of a biologically active peptide while retaining its activity, include a method that involves treating the gene with a mutagen and a method that involves selective cleavage of the gene, removal, substitution, insertion or addition of the selected nucleotide, and then ligation of the cleaved fragments, in addition to the above-described site-directed mutagenesis.

The TM2 mutant may also be a protein comprising an amino acid sequence having at least 80%, preferably 85% or more, 90% or more, 95% or more, 96% or more, 97% or more, 98% or more, or 99% or more, and more preferably 99.2% or more amino acid identity to the amino acid sequence of SEQ ID NO: 2 and having a biotin-binding activity similar to that of TM2.

The percent identity between two amino acid sequences may be determined by visual inspection and mathematical calculation. Alternatively, the percent identity between two protein sequences may be determined through comparison of sequence information using a GAP computer program available from the University of Wisconsin Genetics Computer Group (UWGCG) based on the algorithm by Needleman, S. B. and Wunsch, C. D. (J. Mol. Biol., 48: 443-453, 1970). Preferred default parameters of the GAP program include: (1) scoring matrix: blosum62 as described in Henikoff, S. and Henikoff, J. G., (Proc. Natl. Acad. Sci. USA, 89: 10915-10919, 1992); (2) 12 gap weights; (3) 4 gap length weights; and (4) no penalty for terminal gaps.

Any other program used by those skilled in the art may also be used for comparison of the sequences. The percent identity can be determined by, for example, comparison with the sequence information using a BLAST program described in Altschul et. al., (Nucl. Acids Res., 25, pp. 3389-3402, 1997). This program is available from the website of National Center for Biotechnology Information (NCBI) or DNA Data Bank of Japan (DDBJ) on the Internet. The conditions (parameters) for identity search by the BLAST program are described in detail on these sites. Although these parameters can be partially modified if necessary, search is generally carried out with the default values. Alternatively, the percent identity between two amino acid sequences may be determined using a program such as genetic information processing software GENETYX Ver. 7 (available from Genetyx Corporation) or FASTA algorithm, wherein search may be carried out with the default values.

The percent identity between two nucleotide sequences can be determined by visual inspection and mathematical calculation or preferably through comparison of sequence information using a computer program. A typical preferred computer program is a version 10.0 program "GAP", Wisconsin package of Genetics Computer Group (GCG, Madison, Wis.) (Devereux, et al., (1984), Nucl. Acids Res., 12: 387). The use of the "GAP" program enables comparison between two amino acid sequences and comparison between a nucleotide sequence and an amino acid sequence, in addition to comparison of two nucleotide sequences. The preferred default parameters for the "GAP" program include: (1) the GCG implementation of a unary comparison matrix (containing a value "1" for identities or "0" for non-identities) for nucleotides, and the weighted amino acid comparison matrix of Gribskov and Burgess, Nucl. Acids Res., 14: 6745, 1986, as described in Schwartz and Dayhoff, eds., "Atlas of Polypeptide Sequence and Structure," National Biomedical Research Foundation, pp. 353-358, 1979, or other comparable comparison matrices; (2) a penalty "30" for each gap for amino acids and an additional penalty "1" for each symbol in each gap, or a penalty "50" for each gap for nucleotide sequences and an additional penalty "3" for each symbol in each gap; (3) no penalty for end gaps; and (4) no maximum penalty for long gaps. Other sequence comparison programs used by those skilled in the art can also be used. For example, the BLASTN program, version 2.2.7, which is available via the National Library of Medicine (US) website: http://www.ncbi.nlm.nih.gov/blast/b12seq/b1s.html, or the UW-BLAST 2.0 algorithm can be used. Setting of the standard default parameters for the UW-BLAST 2.0 is described at the following Internet site: http://blast.wustl.edu. In addition, the BLAST algorithm uses the BLOSUM62 amino acid scoring matrix, and optional parameters that can be used are as follows: (A) inclusion of a filter to mask segments of the query sequence having low compositional complexity (determined by the SEG program of Wootton and Federhen (Computers and Chemistry, 1993); also see Wootton and Federhen, 1996, "Analysis of compositionally biased regions in sequence databases," Methods Enzymol., 266: 544-71) or segments consisting of short-periodicity internal repeats (determined by the XNU program of Claverie and States (Computers and Chemistry, 1993)), and (B) a statistical significance threshold for reporting matches against database sequences or E-score (the expected probability of matches being found merely by chance, in accordance with the statistical model (Karlin and Altschul, 1990); if the statistical significance ascribed to a match is greater than the E-score threshold, the match is not reported.); preferred E-score threshold values are 0.5, or in order of increasing preference, 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

The TM2 mutant may also be a protein encoded by a nucleic acid comprising a nucleotide sequence which hybridizese with the complementary strand of the nucleotide sequence of SEQ ID NO: 1 under stringent conditions and having binding activity similar to that of TM2.

As used herein, the term "under stringent conditions" refers to that hybridization occurs under moderately or highly stringent conditions. Specifically, moderately stringent conditions can be readily determined by those having ordinary skill in the art, e.g., on the basis of the length of DNA. The basic conditions are set forth by Sambrook, et al., Molecular Cloning: A Laboratory Manual, 3rd edition, chapter 6, Cold Spring Harbor Laboratory Press, 2001 and include the use of a prewashing solution of 5×SSC, 0.5% SDS, and 1.0 mM EDTA (pH 8.0), hybridization conditions of about 50% formamide, 2×SSC to 6×SSC, preferably 5×SSC to 6×SSC, and 0.5% SDS at about 42° C. (or other similar hybridization solutions, such as Stark's solution, in about 50% formamide at about 42° C.), and washing conditions of, for example, about 50° C. to 68° C., 0.1 to 6×SSC, and 0.1% SDS. Preferably, moderately stringent conditions include hybridization conditions (and washing conditions) at about 50° C., 6×SSC, and 0.5% SDS. Highly stringent conditions can also be readily determined by those skilled in the art, e.g., on the basis of the length of DNA.

In general, such highly stringent conditions include hybridization at higher temperatures and/or lower salt concentrations than the moderately stringent conditions (for example, hybridization in the presence of about 0.5% of SDS at about 65° C., with 6×SSC to 0.2×SSC, preferably 6×SSC, more preferably 2×SSC, more preferably 0.2×SSC or 0.1×SSC) and/or washing, and also include the hybridization conditions defined above with washing at about 65° C. to 68° C., 0.2×SSC or 0.1×SSC, and 0.1% SDS. With regard to the buffer solution for use in hybridization and washing, SSPE (1×SSPE: 0.15 M NaCl, 10 mM $NaH_2PO_4$, and 1.25 mM EDTA; pH 7.4) can be substituted for SSC (1×SSC: 0.15 M NaCl and 15 mM sodium citrate). The washing is performed for about 15 min to 1 hour after completion of the hybridization.

A commercially available hybridization kit including a probe that is not a radioactive substance can also be used. Specifically, hybridization with an ECL direct labeling & detection system (manufactured by Amersham) is available. For example, stringent hybridization is performed using the hybridization buffer included in the kit to which a blocking reagent and NaCl are added in concentrations of 5% (w/v) and 0.5 M, respectively, under the following conditions: at 42° C. for 4 hours and washing twice in 0.4% SDS, 0.5×SSC at 55° C. for 20 min and once in 2×SSC at room temperature for 5 min.

The biotin-binding activity of a TM2 mutant can be determined by any known method, e.g., the fluorescent biotin-based process as described in Kada, et al., (Biochim.

Biophys. Acta, 1427: 33-43 (1999)). This process is an assay system utilizing a property that the fluorescent intensity of fluorescent biotin is quenched by binding of the fluorescent biotin to the biotin-binding site of a biotin-binding protein. Alternatively, the biotin-binding activity of a mutant protein also can be evaluated using a sensor that can measure the binding between the protein and biotin, such as a biosensor, e.g., BIAcore, based on a surface plasmon resonance principle. Alternatively, the activity can also be evaluated by other methods, e.g., a method using HABA (2-(4'-Hydroxyazobenzene) Benzoic Acid) or a method using biotinylated HRP (horse radish peroxidase).

Modified Tamavidin of the Present Invention having Improved Heat Resistance

The modified TM2 of the present invention is a protein comprising an amino acid sequence represented by SEQ ID NO: 2, an amino acid sequence having one or more amino acid mutations in the sequence represented by SEQ ID NO: 2, or an amino acid sequence having an identity of not less than 80% to the sequence of SEQ ID NO: 2, and maintaining the structure of protein, preferably having bition-binding activity, wherein an asparagine residue at position 115 of SEQ ID NO 2 is replaced with cysteine.

Furthermore, the modified TM2 of the present invention is characterized in that the amino acid residue corresponding to asparagine residue at position 115 of SEQ ID NO: 2 in wild-type TM2 or a mutant TM2 is replaced with cysteine.

The heat resistant modified tamavidin 2 of the present invention was prepared as follows.

A gene was prepared by designing a mutant in which N115 of tamavidin 2 was replaced with cysteine (Cys). This gene was inserted into an expression vector, and was expressed in *E. coli*. The expressed mutant (TM2 N115C) as soluble protein was expressed at a high level, like tamavidin 2 (TM2). Purification by affinity chromatography on iminobiotin agarose was conducted to give about 14 mg of TM2 N115C from 300 mL of culture medium.

The prepared modified tamavidin 2 was analysed as follows.

The biotin-binding activity of the purified TM2 N115C was determined by BIAcore (the analyser for interactions of biological samples). The results demonstrated that the TM2 N115C had a significantly strong biotin-binding activity at the same level as the TM2. Furthermore, the TM2 N115C, TM2, avidin, neutravidin, and streptavidin were treated at 99.9° C. for 30 to 32 min, were immobilized on a microplate, and were reacted with the biotinylated Horse Radish Peroxidase (HRP) to determine their HRP activity. The results showed that, while almost no activity was detected for avidin, neutravidin, and streptavidin, TM2 retained 12% of its initial biotin-binding activity, and further TM2 N115C had the almost full activity (92% to 100%). It is surprising that the TM2 N115C retains the activity almost completely after being treated at 99.9° C. for about 30 min, considering the reports that the I117C mutant of avidin loses the activity completely after a treatment at 99.9° C. for 5 min (Nordlund et al., (2003), J. Biol. Chem., 278: 2479-2483), and that the activity of the H127C mutant of streptavidin is reduced to 20% at 95° C. for 10 min (Reznik et al., (1996), Nat. Biotechnol., 14: 1007-1011). This heat resistance is comparable to that of the above-described avidin mutant, ChiAVD (I117Y) constructed by chimerization of avidin (Hytonen et al., (2005), J. Biol. Chem., 280: 10228-10233).

Throughout the specification, "tamavidin 2 (TM2)" is as already defined above.

Such modified TM2 maintains the structure of protein even after the heat treatment. The modified TM2 of the present invention preferably maintains 75% or more, 80% or more, more preferably 85% or more, 90% or more, 92% or more, and most preferably 95% or more of its biotin-binding activity prior to the treatment. The temperature of the heat treatment is at least 90° C. or more, preferably 93° C. or more, 95° C. or more, 97° C. or more, 98° C. or more, 99° C. or more, and most preferably 99.9° C. The upper limit of the temperature of the heat treatment is not over 100° C. The time for the heat treatment is at least 10 min, preferably 20 min or more, 30 min or more, most preferably 32 min.

Furthermore, even after the treatment in an aprotic polar organic solvent, such modified TM2 maintains at least 50% of the biotin-binding activity prior to the treatment. The concentration of the organic solvent used in the treatment with an aprotic polar organic solvent is at least 60% or more, preferably 65% or more, 70% or more, 75% or more, and most preferably 80%. The upper limit of the concentration of the organic solvent is below 90%. The time for the treatment in the aprotic polar organic solvent is at least 10 min, preferably 20 min or more, most preferably 30 min or more. These treatments can be carried out at, but not limited to, room temperature (25° C.).

Examples of the aprotic polar organic solvent used herein may include, but not limited to, dimethyl sulfoxide (DMSO), tetrahydrofuran (THF), acetone, acetonitrile, and N,N-dimethylformamide (DMF). Particularly preferred aprotic polar solvent is DMSO.

As used herein, the phrase "maintaining the structure of protein" after the heat treatment means that the modified TM2 of the present invention maintains the same protein conformation with that of the original TM2 even after the heat treatment. The term "protein conformation" refers to secondary or higher protein structure, preferably tertiary or quaternary structure.

As used herein, the phrase "maintaining the biotin-binding activity of at least 50%" means that the modified TM2 of the present invention maintains the biotin activity, which is measured after the heat treatment and/or the organic solvent treatment, of at least 50% of the activity prior to the treatment. The upper limit of the temperature of the heat treatment is 100° C.

Furthermore, preferably the modified TM2 of the present invention, which is a protein comprising an amino acid sequence having an identity of not less than 90% to the amino acid sequence represented by SEQ ID NO: 2 and having a biotin-binding activity, is characterized in that an asparagine residue at position 115 of SEQ ID NO: 2 is replaced with cysteine. More preferably, the modified TM2 of the present invention (TM2 N115C) is characterized in that an asparagine residue at position 115 of SEQ ID NO: 2 is replaced with cysteine (SEQ ID NO: 4).

Amino Acid Residues that are Desirably not Modified in the Modified TM2 of the Present Invention The modification of amino acid residues in the modified TM2 of the present invention should not affect the biotin-binding ability. In light of this, it is preferred that four tryptophan residues (W69, W80, W96, and W108) in the amino acid sequence of SEQ ID NO: 2 should not be modified in the mutant of tamavidin 2, although this is nonatributive. Alternatively, in the case where these amino acid residues are modified, the amino acids are preferably replaced with one having a similar property or structure, for example, phenylalanine (F). Furthermore, it is desirable that amino acid residues (N14, S18, Y34, S36, S76, T78, and D116) that may interact directly with biotin are also not modified. Alternatively, in the modification of these amino acid residues, the amino acids are preferably replaced with one having a similar property or structure so as to maintain the binding with biotin. For example, asparagine (N14) is replaced with glutamine (Q) or aspartic acid (D), preferably aspartic acid; aspartic acid (D40) is replaced with asparagine (N); serine (S18, S36, or S76) is replaced with threonine (T) or tyrosine (Y), preferably threonine; tyrosine (Y34) is replaced with serine (S), threonine (T), or phenylalanine (F), preferably phenylalanine; threonine (T78) is replaced with serine (S) or tyrosine (Y), preferably serine; and aspartic acid (D116) is replaced with glutamic acid (E) or asparagine (N), preferably asparagine.

Method for Modification of Amino Acid

The modified TM2 of the present invention can be obtained through modification of amino acid(s) of TM2 by any known method that causes mutation in an amino acid sequence without any particular limitation. Preferably, modification is performed in the nucleotide sequence of nucleic acid encoding the modified protein of the present invention.

For example, in order to modify an amino acid at a specific position of an amino acid sequence, for example, a method employing PCR can be used (Higuchi, et al., (1988), Nucleic Acid Res., 16: 7351-7367; Ho, et al., (1989), Gene, 77: 51-59). Specifically, a desired mutant can be obtained by PCR using a primer containing a mismatch codon for a target mutation to produce DNA encoding the desired mutant and expressing the DNA.

A mutant by deletion, substitution, insertion, and/or addition of amino acid(s) can be produced by such a known method as implementing site-directed mutagenesis in DNA encoding a wild-type protein.

Nucleic Acid Encoding Modified TM2 Protein

The present invention provides a nucleic acid encoding the modified TM2 protein of the present invention. In the nucleotide sequence of such a nucleic acid, the nucleotide sequence (SEQ ID NO: 1) encoding wild-type TM2 protein is modified to a nucleotide sequence encoding the modified amino acids of the modified TM2 protein. Any modified nucleotide sequence that encodes the amino acid or amino acids after modification can be used without limitation. Examples of the modified nucleotide sequence include nucleic acids having modified nucleotide sequences for modification of the present invention, wherein the nucleic acids are those comprising the nucleotide sequence of SEQ ID NO: 1 (hereinafter referred to as "TM2 gene") or those which hybridizes with the complementary strands thereof under stringent conditions and encoding proteins having proper biotin-binding activity for binding to biotin.

Preferably, the nucleic acid of the present invention encodes the amino acid sequence of SEQ ID NO: 4. More preferably, the nucleic acid of the present invention includes the nucleotide sequence of SEQ ID NO: 3.

Vector Containing Nucleic Acid of the Present Invention

The present invention provides a vector containing a nucleic acid encoding a modified TM2 protein, preferably an expression vector for expressing a modified TM2 protein.

The nucleic acid encoding the modified TM2 protein of the present invention is as described in the section "Nucleic acid encoding modified TM2 protein", which can be used without limitation. It is desirable that a promoter functioning in a desired host and a terminator be placed upstream and downstream, respectively, of the nucleic acid encoding the modified TM2 protein.

The vector of the present invention is preferably an expression vector. The expression vector includes a unit for replication in a desired host, for example, a replication origin, and may include a drug-resistant marker gene for selecting a desired host cell, in addition to an expression unit (promoter, modified TM2-encoding region, and terminator) as described above. Any host can be used without limitation, and preferred is *E. coli*. The expression vector may contain an appropriate expression regulatory system such as a lactose repressor system in *E. coli*.

Modified TM2-Immobilized Support

The present invention provides a support to which the modified TM2 protein of the present invention is immobilized.

Any known material constituting a support can be used, and examples thereof include, but are not limited to, cellulose, Teflon(™), nitrocellulose, highly crosslinked agarose, dextran, chitosan, polystyrene, polyacrylamide, polyester, polycarbonate, polyamide, polypropylene, nylon, polyvinylidene difluoride, latex, silica, glass, glass fiber, gold, platinum, silver, copper, iron, stainless steel, ferrite, silicon wafer, high density polyethylene, polyethyleneimine, polylactic acid, resin, polysaccharides, carbon, and combinations thereof. Materials having a certain level of strength and stable composition with low non-specific binding are preferred.

Examples of the shape of the solid support include, but not limited to, beads, magnetic beads, thin films, microcapillary tubes, filters, plates, microplates, carbon nanotubes, and sensor chips. A planar solid support, such as a thin film or a plate, may be provided with, for example, pits, grooves, filter bottoms, as known in the art.

In one embodiment of the present invention, the beads can have a spherical diameter in the range of about 25 nm to about 1 mm. In a preferred embodiment, the beads have a diameter in the range of about 50 nm to about 10 μm. The size of the beads can be selected depending on specific application.

The immobilization of the protein to the support is not particularly limited and can be achieved by a known method for immobilizing a protein to a support. Specific method for immobilization can be appropriately selected by those skilled in the art depending on the type of the support.

The Method for Heat Purification for Modified TM2

Furthermore, the present invention provides a method for heat purification of the modified TM2 protein of the present invention. The modified TM2 protein of the present invention has remarkable heat resistance, which allows it to maintain the original structure without denaturation even if it was subjected to heat treatment under severe conditions causing denaturation of most proteins. Then, the sample containing the modified TM2 protein of the present invention is subjected to heat treatment of at least 90° C. for at least 10 min to collect the intact protein with no denaturation, and thus the protein can be purified. The method including the heat treatment is used for not only the purification of the modified TM2 protein, but also used for the purpose of separation, concentration, capture, and detection of the protein.

The condition for heat treatment herein is at least 90° C. at least for 10 min, preferably for 20 min, more preferably 30 min; preferably 95° C. for 30 min, 98° C. for 30 min, 99° C. for 30 min; especially preferably 99.9° C. for 30 min. Specific examples of the means for collecting the protein having no denaturation include, but not limited to, pelleting the denatured protein by centrifugation and collecting the supernatant, filtration, and molecular sieve chromatography.

The Method of Detecting Modified TM2 using an Organic Solvent

Furthermore, the present invention provides a method of purifying a biotin-linked substance in a system containing organic solvent using the modified TM2 of the present invention having organic solvent resistance. The method of the present invention includes the following steps:
1) contacting the modified TM2-binding support with a biotin-linked substance whereby the biotin-linked substance is bound to the support;
2) washing off contaminants which are not bound to the support with a solution containing 60% to 80% of aprotic polar solvent;
3) collecting the biotin-linked substance which is bound to the support. The method including the washing process using aprotic polar solvent can be used for the purpose of not only purification but also separation, concentration, capture, and detection of the biotin-linked substance.

The term "biotin-linked substance", as used herein, refers to a substance which is linked to biotin either directly or indirectly. Direct linking between biotin and a substance can be achieved by covalent bonding. Indirect linking between biotin and a substance can be achieved by establishing a further linkage between the substance and a ligand covalently attached to biotin, through covalent bonding, ionic bonding, hydrogen bonding or hydrophobic interaction. Specific examples of indirect linking include conjugation of an antigen molecule using a biotinylated antibody through antigen-antibody reaction.

For example, in the case where the desired protein antigen is purified, an analyte containing the protein antigen is firstly incubated in an appropriate buffer solution with a biotinylated antibody capable of specifically binding the protein antigen. Antibody biotinylation can be achieved, for example, with a kit commercially available from Pierce or other manufacturers. Then, the modified TM2-attached solid support (e.g., magnetic beads) of the present invention is added and mixed. The complexes of (protein antigen)—(biotin-modified TM2 of the present invention)—(magnetic bead) are then coagulated with a magnet and the supernatant is removed, followed by washing with an appropriate buffer solution containing aprotic polar solvent. The magnet is then removed and the complexes are suspended in a desired buffer solution to complete purification of the protein antigen. Thus, the method of the present invention enables washing in a buffer solution containing aprotic polar solvent to allow for effective purification of the protein antigen with reduced contaminants.

The concentration of aprotic polar solvent in the solution used for washing herein ranges from at least 60% to 80%, preferably from 65% to 75%, more preferably. 70%. Preferred aprotic polar solvent is dimethylsulfoxide.

TM2 N115C of the present invention, which has high resistance to dimethylsulfoxide, can be used for the reaction with such a biotinylated substance as a lipid-containing one that has low water solubility and is only soluble in high-concentration (60% to 80%) dimethylsulfoxide,

EXAMPLES

1. Design of Modified Tamavidin 2 Directed to the Improvement in Heat Resistance A TM2 N115C mutant, which was formed by replacing N115 in tamavidin 2 with cysteine (Cys), was designed.

2. Construction of a Modified Tamavidin 2 Gene and its Expression in *E. coli*

2-1. Gene Construction

PCR was performed using a plasmid (TM2/pTrc99A) (WO02/072817), i.e., a tamavidin 2 gene incorporated into an expression vector for *E. coli* (pTrc99A), as a template. The sequences of the primers (SEQ ID NO: 5 to SEQ ID NO: 8) used are shown in Table 1.

TABLE 1

| [Table 1] Primers for constructing TM2 N115C gene | | |
|---|---|---|
| Name | Sequence (5'-3') | Length |
| Tm2NtermPci | AAA <u>ACATGT</u> CAGACGTTCAATCTTC | 25 mer (SEQ ID NO: 5) |
| Tm2CtermBam | TTT <u>GGATCC</u> *TTA*CTTCAACCTCGGTGCG | 28 mer (SEQ ID NO: 6) |
| TM2 N115C FW | CTTGTGGGGtgtGATTCGTTT | 21 mer (SEQ ID NO: 7) |
| TM2 N115C RV | AAACGAATCacaCCCCACAAG | 21 mer (SEQ ID NO: 8) |

Underlined segments indicate restriction enzyme sites, and bold italic segmenst indicate the start and stop condons. Replaced condons are shown in lowercase letters.

TM2N115C

PCRs were performed, with a plasmid TM2/pTrc99A containing TM2 as a template, and a primer combination of Tm2NtermPci and TM2 N115C RV or a primer combination of Tm2CtermBam and TM2 N115C FW separately. The obtained product was subjected to agarose gel electrophoresis on low melting point agarose and purified from the gel. The second PCR (overlapping PCR) was performed with a primer combination of Tm2NtermPci and Tm2CtermBam using the two purified PCR products as the templates. PCR was performed in 50 μL reaction solution containing plasmid, 10× PyroBest buffer (TaKaRa) (5 μL), 2.5 mM dNTPs (4 μL), primers (each 25 pmoles), PyroBest DNA polymerase (TaKaRa) (0.5 μL) under the following conditions: 1 cycle of 96° C. for 3 min; 15 cycles of 96° C. for 1 min, 55° C. for 1 min, and 72° C. for 1 min; and 1 cycle of 72° C. for 6 min.

The resulting PCR product was cloned into the vector pCR4 Blunt TOPO (Invitrogen). Plasmid was introduced into *E. coli* TB1 by electroporation and the plasmid DNA was extracted in a usual manner (Sambrook et al., 1989, Molecular Cloning, A laboratory manual, 2nd edition) to determine the nucleotide sequence of the PCR product from both ends.

The clone confirmed to contain the desired mutation was digested with PciI and BamHI and subjected to electrophoresis on low melting point agarose to be purified. The *E. coli* expression vector was prepared by digestion of pTrc99A with restriction enzymes, NcoI and BamHI. The DNA fragments and the vecor which were treated with the restriction enzymes were ligated with a Ligation kit (Takara). The ligation product was transformed into *E. coli* BL21 and clones containing inserted genes were determined by colony PCR to be used in expression experiments.

2-2. E. coli Expression

A single colony of *E. coli* incorporating tamavidin 2 and the tamavidin 2 mutant prepared as described above was inoculated into a LB medium containing antibiotic ampicilline (final concentration: 100 μg/mL), and cultured with shaking at 37° C. overnight. The product was then inoculated into a LB medium containing ampicilline, and cultured at 37° C. for 2 hours, followed by addition of isopropyl-β-D(−)-thiogalactopyranoside (IPTG) up to a final concentration of 1 mM to induce expression, and cultured for additional 5 to 6 hours.

The cells are then collected by centrifugation, and suspended in 50 mM CAPS (pH 12) containing 50 mM NaCl. The suspension was sonicated, followed by centrifugation, and 2-iminobiotin agarose (SIGMA) was added to the resulting supernatant. The mixture was adjusted to pH 12 with NaOH, and incubated at room temperature. The mixture was packed in an open column and the column was washed well with 10 column volumes of 50 mM CAPS (pH 12) containing 500 mM NaCl. The protein was then eluted with 5 column volumes of 50 mM $NH_4OAc$ (pH 4). The eluted fractions were dialyzed in 0.1 M HEPES (pH 7.4) containing 50 mM NaCl to be used in the following analysis. About 14 mg of the purified protein TM2 N115C was obtained from 300 mL of the culture medium. The purity of the resulting TM2 N115C was 95% or more.

3. Heat Resistance Test of Modified Tamavidin 2

3-1. Fluorescent Biotin Assay

The heat resistance of purified TM2 and TM2 N115C were analysed using their binding activity to fluorescent biotin. Specifically, the biotin-binding ability of TM2 N115C at high temperature was compared with that of TM2 based on the property of fluorescent biotin to lose its fluorescence intensity when bound to a biotin-binding site of a biotin-binding protein.

Each purified protein was diluted with 20 mM KPi (pH 7) to have a concentration of about 0.1 μg/μL and the resulting solutions were heated at room temperature, 50° C., 60° C., 70° C., 80° C., 90° C., and 99° C. for 20 min, respectively. Each solution after the heat treatment was added in a stepwise manner in a variable amount into 150 μL, assay buffer (50 mM $Na_2PO_4$, 100 mM NaCl, 1 mM EDTA (pH 7.5)). These solutions were each mixed with 50 pmol fluorescent biotin solution (biotin-4-fluorescein: Molecular probe) and allowed to react at room temperature for 20 min, followed by measuring the fluorescence intensity at Ex=460 nm, and Em=525 nm with Infinite M200 (TECAN). Furthermore, for consideration of the effect of disulfide (S-S) binding, 100 mM DTT was added to the diluted protein solution followed by being left at room temperature for 30 min. The mixture was then heated in the steps as described above to determine fluorescent biotin.

As a result, the biotin-binding activity of TM2 to fluorescent biotin declined at 90° C., whereas most of the activity of TM2 N115C was maintained at 99.9° C. The temperature at which the fluorescent intensity is reduced to 50% of that of the unheated sample was at least 99.9° C. for TM2 N115C vs. 85° C. for TM2. The binding activity of TM2 N115C was maintained, although slightly weakened, after a prolonged heat treatment at 99.9° C. for 60 min, while almost no binding activity of TM2, avidin, and streptavidin remained after a heat treatment at 99.9° C. for 60 min.

The activity of TM2 N115C was found to be weakened after DTT treatment at 90° C. for 20 min. This indicates that the disulfide bond (S-S) formed in TM2 N115C by the newly inserted cysteine residue probably contributes to an improvement in heat resistance.

3-2. Binding Assay with Biotinylated HRP

Figure 2:
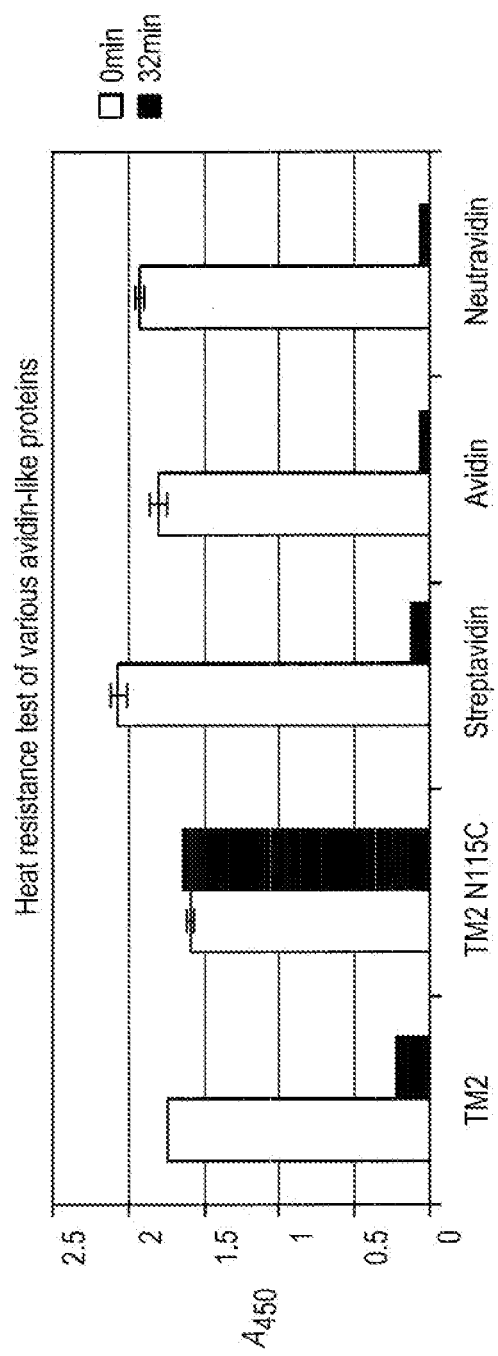
FIG. 2 is a graph showing the biotin-binding ability after a heat treatment at 99.9° C. for 32 min of modified TM2 N115C of the present invention, TM2, and various avidin-like proteins (streptavidin, avidin, and neutravidin).
Figure 3A:
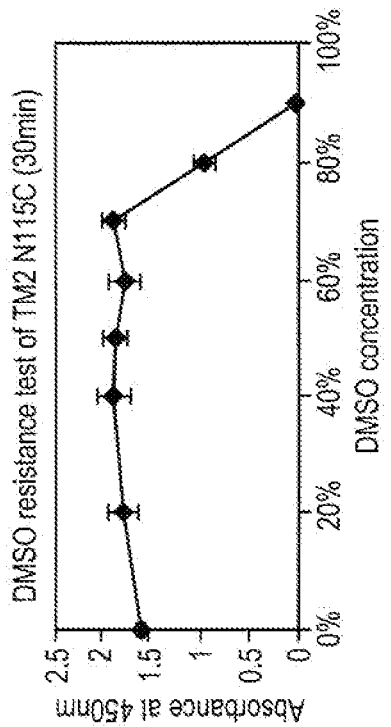
FIG. 3 is a graph showing the biotin-binding ability of modified TM2 N115C of the present invention, TM2, and various avidin-like proteins (streptavidin and avidin) after being mixed with biotinylated magnetic beads in the presence of dimethyl sulfoxide. They were mixed with various concentrations of dimethyl sulfoxide for 30 min.
Figure 3B:
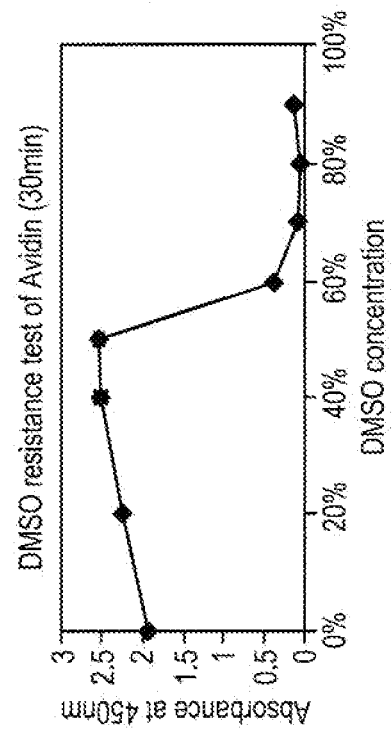
Figure 3C:
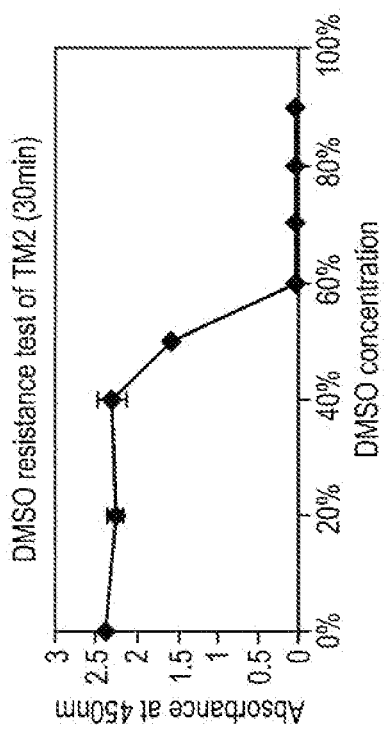
Figure 3D:
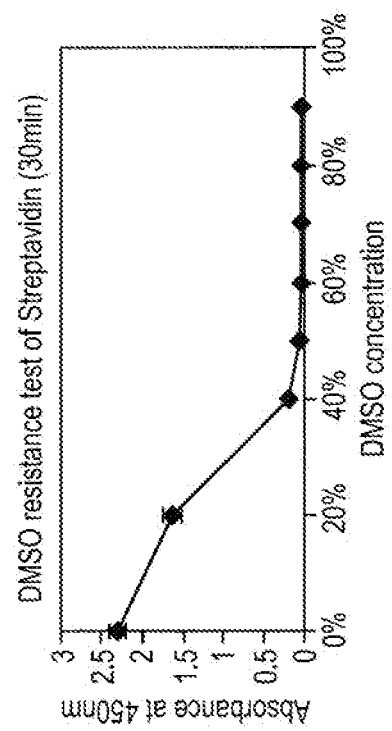

TM2 N115C, TM2, avidin, neutravidin, and streptavidin were treated at 99.9° C. for 1, 2, 4, 10, 20, or 32 min, then were immobilized onto a microplate for hydrophobic bonding (Sumitomo Bakelite Co., Ltd., Type H), and were further reacted with biotinylated horseradish peroxidase (HRP) (VECTOR) to determine HRP activity. FIG. 1 shows the results of the activity of the samples treated at 99.9° C. for 1, 2, 4, 10, and 20 min. FIG. 2 and Table 2 show the results of the activity of the samples processed at 99.9° C. for 32 min. In FIG. 2, white columns represent the results of the unheated samples, and black columns represent the results of the heat-processed samples.

The results demonstrate that avidin, neutravidin, and streptavidin has almost no detective activity after a heat treatment at 99.9° C. for 32 min, whereas TM2 maintained 10 to 12% of the initial activity after such a treatment (40% of the initial activity after a treatment at 99.9° C. for 20 min). Furthermore TM2 N115C maintained almost full (92% to 100%) biotin-binding activity even after a treatment at 99.9° C. for 30 or 32 min (Table 2). The heat resistance of TM2 N115C is significantly higher than that of the previously reported technologies; almost complete loss of the activity of the I117C mutant of avidin after a treatment at 99.9° C. for 5 min (Nordlund et al., (2003), J. Biol. Chem., 278: 2479-2483), and a reduction of the activity of the H127C mutant of streptavidin to 20% at 95° C. for 10 min (Reznik et al. (1996), Nat. Biotechnol., 14: 1007-1011).

TABLE 2

Residual activity after heat treatment
(Binding activity to biotinylated HRP)

| | Heat treatment (99.9° C.) | | | |
|---|---|---|---|---|
| | Experiment 1 | | Experiment 2 | |
| Protein | After 0 min | After 32 min | After 0 min | After 30 min |
| TM2 | 100% | 12% | 100% | 10% |
| TM2 N115C | 100% | 100% | 100% | 92% |
| Streptavidin | 100% | 6% | | |
| Avidin | 100% | 3% | | |
| Neutravidin | 100% | 3% | | |

4. Organic Solvent Resistance Test of Modified Tamavidine 2

4-1. DMSO Resistance Test

Biotinylated magnetic beads were prepared by reacting NHS-$PEG_{12}$-biotin (PIERCE) with Dynabeads M270-Amine (Dynal).

Each of avidin-like protein solutions of a final concentration of 25 μg/mL (TM2 N115C, TM2, avidin, neutravidin, and streptavidin) and the biotinylated magnetic beads were mixed by inversion for 30 min at room temperature (25° C.) in the presence of dimethyl sulfoxide (DMSO) of a final concentration of 0%, 20%, 40%, 50%, 60%, 70%, 80%, and 90%. This operation immobilized the avidin-like protein on the surface of the magnetic beads. The magnetic beads on which the avidin-like proteins were immobilized were washed with 0.2% Tween 20/TBS, and were dispensed in a 96-well plate at an aliquot of 5 μL. Biotinylated HRP (VECTOR), which was diluted into 5000-fold with PBS containing 2% BSA, was added into each well in at an aliquot of 200 μL, followed by mixing with shaking at room temperature for 1 hour. The magnetic beads were then washed to detect the activity of HRP immobilized on the magnetic beads using 1-step Ultra TMB-ELISA (PIERCE)

FIG. 3 shows the results. FIGS. 3A, 3B, 3C, and 3D show the results of TM2, TM2 N115C, streptavidin, and avidin, respectively.

FIG. 3 demonstrates that TM2 N115C maintains the full biotin-binding ability even in the presence of 70% DMSO, and still maintains 50% of the initial biotin-binding ability even in the presence of 80% DMSO, whereas wild-type tamavidin (TM2) and avidin lost most of the biotin-binding ability in the presence of 60% DMSO and streptavidin lost most of the biotin-binding ability in the presence of 40% DMSO.

5. Interaction Between TM2 N115C and Biotin

Analysis of Affinity for Biotin-Lc-BSA

The interaction of TM2 N115C with biotin was analysed using a BIAcore 3000. Table 3 shows the results of the analysis of the interaction of Biotin-Lc-BSA. TM2 N115C was found to have almost the same level of biotin-binding activity as TM2 because TM2 has an association rate constant ka of $(1.0 \pm 0.3) \times 10^6$ $(M^{-1}-S^{-1})$, and a dissociation rate constant kd of $<5 \times 10^{-6}$ $S^{-1}$ (below the detection limit of BIAcore 3000) (Takakura et al., (2009), FEBS J., 276: 1383-1397).

TABLE 3

Binding rate constant (ka) and dissociation rate constant (kd) of the proteins to biotin (Analysis using Biacore)

| Protein | ka ($M^{-1} \cdot S^{-1}$) | kd ($S^{-1}$) |
|---|---|---|
| No heat treatment | | |
| TM2 N115C | $(7.1 \pm 2.9) \times 10^5$ | Below detection limit |
| After heat treatment (90° C., 20 min) | | |
| TM2 | $8.4 \times 10^4$ | $1.5 \times 10^{-5}$ |
| TM2N115C | $1.0 \times 10^6$ | Below detection limit |

Analysis of Affinity for Biotin-Lc-BSA of Protein after Heat Treatment

The test using fluorescent biotin suggests that the fluorescent biotin-binding activity of TM2 N115C does not decrease after a heat treatment at 90° C. for 20 min, whereas the fluorescent biotin-binding activity of TM2 decreases. Then the affinity for Biotin-Lc-BSA of the protein after the heat treatment was determined TM2 solution and TM N115C were each diluted into about 0.6 mg/mL (20 mM KPi (pH 7). Each solution was heated at 90° C. for 20 min to be subjected to centrifugation at 15000 rpm at 4° C. for 10 min. The supernatant was collected and the concentration was determined by $A_{280}$, and then the affinity for Biotin-Lc-BSA was analysed using BIAcore in the same manner as described above.

Table 3 shows the analytical results of the interaction after the treatment at 90° C. with the Biotin-Lc-BSA obtained with BIAcore. TM2 N115C exhibits no decrease in the affinity for biotin even after the treatment at 90° C., whereas TM2 exhibits a decrease in the affinity for biotin after the treatment at 90° C.

The invention claimed is:

1. A modified biotin-binding protein comprising any one of following (a) and (b):
   (a) an amino acid sequence having 1 to 7 amino acid mutations in the amino acid sequence of SEQ ID NO: 2 and having biotin-binding activity, and
   (b) an amino acid sequence having an identity of not less than 95% to the amino acid sequence of SEQ ID NO: 2 and having biotin-binding activity;
   wherein an asparagine residue at position 115 of SEQ ID NO: 2 is replaced with cysteine,
   wherein the modified biotin-binding protein maintains biotin-binding activity of not less than 75% after a heat treatment at 99.9° C. for 30 min, compared with the activity before the treatment, and
   wherein the modified biotin-binding protein maintains biotin-binding activity of not less than 50% after a treatment in 60% aprotic polar organic solvent for 30 min, compared with the activity before the treatment.

2. A modified biotin-binding protein comprising an amino acid sequence represented by SEQ ID NO: 2,
   provided that an asparagine residue at position 115 of SEQ ID NO: 2 is replaced with cysteine,
   wherein the modified biotin-binding protein maintains biotin-binding activity of not less than 75% after a heat treatment at 99.9° C. for 30 min, compared with the activity before the treatment, and
   wherein the modified biotin-binding protein maintains biotin-binding activity of not less than 50% after a treatment in 60% aprotic polar organic solvent for 30 min, compared with the activity before the treatment.

3. The modified biotin-binding protein according to claim 1 or 2, wherein the aprotic polar organic solvent is dimethyl sulfoxide.

4. The modified biotin-binding protein according to claim 1, wherein the modified biotin-binding protein comprises an amino acid having an identity of not less than 98% to the amino acid sequence of SEQ ID NO: 2.

5. A support to which the protein according to claim 1 or 2 is immobilized.

6. A nucleic acid encoding the protein according to claim 1 or 2.

7. A vector containing the nucleic acid according to claim 6.

8. A method for separation, concentration, capture, purification, and/or detection of the protein according to claim 1 or 2, which comprises the following steps:
   1) heat-treating a sample containing the protein at a temperature of at least 90° C. for at least 10 min; and
   2) collecting the protein which does not receive heat-denature in step 1) to thereby separate, concentrate, capture, or purify the protein, and/or detect the substance.

9. A method for separation, concentration, capture, purification and/or detection of a biotin-linked substance, which comprises the following steps:
   1) contacting the support according to claim 5 with a biotin-linked substance, whereby the biotin-linked substance is bound to the support;
   2) washing off contaminants which are not bound to the support with a solution containing 60% to 80% of aprotic polar organic solvent; and
   3) collecting the biotin-linked substance which is bound to the support to thereby separate, concentrate, capture or purify the substance and/or detect the substance.

10. The method according to claim 9, wherein the aprotic polar organic solvent is dimethyl sulfoxide.

* * * * *

SEQUENCE LISTING

```
<160> NUMBER OF SEQ ID NOS: 8

<210> SEQ ID NO 1
<211> LENGTH: 426
<212> TYPE: DNA
<213> ORGANISM: Pleurotus cornucopiae
<220> FEATURE:
<221> NAME/KEY: CDS
<222> LOCATION: (1)..(426)

<400> SEQUENCE: 1 atg tca gac gtt caa tct tca ctc acc gga acc tgg tac aat gaa ctc      48
Met Ser Asp Val Gln Ser Ser Leu Thr Gly Thr Trp Tyr Asn Glu Leu
1               5                   10                  15 aac tcc aag atg gaa ttg act gca aac aaa gac ggt act ctc act gga      96
Asn Ser Lys Met Glu Leu Thr Ala Asn Lys Asp Gly Thr Leu Thr Gly
            20                  25                  30 aag tac ctc tcc aaa gtt ggg gat gtc tac gtg ccc tac cca ctc tct     144
Lys Tyr Leu Ser Lys Val Gly Asp Val Tyr Val Pro Tyr Pro Leu Ser
        35                  40                  45 ggt cgc tat aac ctc caa ccc ccc gcg gga caa ggc gtc gct ctt ggg     192
Gly Arg Tyr Asn Leu Gln Pro Pro Ala Gly Gln Gly Val Ala Leu Gly
    50                  55                  60 tgg gcg gta tcc tgg gag aac agt aaa att cat tcc gct acg aca tgg     240
Trp Ala Val Ser Trp Glu Asn Ser Lys Ile His Ser Ala Thr Thr Trp
65                  70                  75                  80 agc gga cag ttc ttc tct gag tcg tct cca gtg att ctt act cag tgg     288
Ser Gly Gln Phe Phe Ser Glu Ser Ser Pro Val Ile Leu Thr Gln Trp
                85                  90                  95 ttg ttg tca tcg agc act gcg cgt ggg gac gta tgg gaa tcc aca ctt     336
Leu Leu Ser Ser Ser Thr Ala Arg Gly Asp Val Trp Glu Ser Thr Leu
```

```
                 100                 105                 110
gtg ggg aat gat tcg ttt aca aag acg gcg ccg act gag cag cag atc        384
Val Gly Asn Asp Ser Phe Thr Lys Thr Ala Pro Thr Glu Gln Gln Ile
            115                 120                 125 gct cat gct caa ctc cat tgt cgc gca ccg agg ttg aag taa                426
Ala His Ala Gln Leu His Cys Arg Ala Pro Arg Leu Lys
        130                 135                 140

<210> SEQ ID NO 2
<211> LENGTH: 141
<212> TYPE: PRT
<213> ORGANISM: Pleurotus cornucopiae

<400> SEQUENCE: 2

Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ser Lys Val Gly Asp Val Tyr Val Pro Tyr Pro Leu Ser
        35                  40                  45

Gly Arg Tyr Asn Leu Gln Pro Pro Ala Gly Gln Gly Val Ala Leu Gly
    50                  55                  60

Trp Ala Val Ser Trp Glu Asn Ser Lys Ile His Ser Ala Thr Thr Trp
65                  70                  75                  80

Ser Gly Gln Phe Phe Ser Glu Ser Ser Pro Val Ile Leu Thr Gln Trp
                85                  90                  95

Leu Leu Ser Ser Ser Thr Ala Arg Gly Asp Val Trp Glu Ser Thr Leu
            100                 105                 110

Val Gly Asn Asp Ser Phe Thr Lys Thr Ala Pro Thr Glu Gln Gln Ile
        115                 120                 125

Ala His Ala Gln Leu His Cys Arg Ala Pro Arg Leu Lys
    130                 135                 140

<210> SEQ ID NO 3
<211> LENGTH: 426
<212> TYPE: DNA
<213> ORGANISM: Artificial Sequence
<220> FEATURE:
<223> OTHER INFORMATION: Synthetic construct: TM2 N115C
<220> FEATURE:
<221> NAME/KEY: CDS
<222> LOCATION: (1)..(426)

<400> SEQUENCE: 3 atg tca gac gtt caa tct tca ctc acc gga acc tgg tac aat gaa ctc        48
Met Ser Asp Val Gln Ser Ser Leu Thr Gly Thr Trp Tyr Asn Glu Leu
1               5                   10                  15 aac tcc aag atg gaa ttg act gca aac aaa gac ggt act ctc act gga        96
Asn Ser Lys Met Glu Leu Thr Ala Asn Lys Asp Gly Thr Leu Thr Gly
            20                  25                  30 aag tac ctc tcc aaa gtt ggg gat gtc tac gtg ccc tac cca ctc tct        144
Lys Tyr Leu Ser Lys Val Gly Asp Val Tyr Val Pro Tyr Pro Leu Ser
        35                  40                  45 ggt cgc tat aac ctc caa ccc ccc gcg gga caa ggc gtc gct ctt ggg        192
Gly Arg Tyr Asn Leu Gln Pro Pro Ala Gly Gln Gly Val Ala Leu Gly
    50                  55                  60 tgg gcg gta tcc tgg gag aac agt aaa att cat tcc gct acg aca tgg        240
Trp Ala Val Ser Trp Glu Asn Ser Lys Ile His Ser Ala Thr Thr Trp
65                  70                  75                  80 agc gga cag ttc ttc tct gag tcg tct cca gtg att ctt act cag tgg        288
```

```
Ser Gly Gln Phe Phe Ser Glu Ser Ser Pro Val Ile Leu Thr Gln Trp
                85                  90                  95 ttg ttg tca tcg agc act gcg cgt ggg gac gta tgg gaa tcc aca ctt      336
Leu Leu Ser Ser Ser Thr Ala Arg Gly Asp Val Trp Glu Ser Thr Leu
            100                 105                 110 gtg ggg tgt gat tcg ttt aca aag acg gcg ccg act gag cag cag atc      384
Val Gly Cys Asp Ser Phe Thr Lys Thr Ala Pro Thr Glu Gln Gln Ile
        115                 120                 125 gct cat gct caa ctc cat tgt cgc gca ccg agg ttg aag taa              426
Ala His Ala Gln Leu His Cys Arg Ala Pro Arg Leu Lys
    130                 135                 140
```

<210> SEQ ID NO 4
<211> LENGTH: 141
<212> TYPE: PRT
<213> ORGANISM: Artificial Sequence
<220> FEATURE:
<223> OTHER INFORMATION: Synthetic Construct: TM2 N115C

<400> SEQUENCE: 4

```
Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ser Lys Val Gly Asp Val Tyr Val Pro Tyr Pro Leu Ser
        35                  40                  45

Gly Arg Tyr Asn Leu Gln Pro Pro Ala Gly Gln Gly Val Ala Leu Gly
    50                  55                  60

Trp Ala Val Ser Trp Glu Asn Ser Lys Ile His Ser Ala Thr Thr Trp
65                  70                  75                  80

Ser Gly Gln Phe Phe Ser Glu Ser Ser Pro Val Ile Leu Thr Gln Trp
                85                  90                  95

Leu Leu Ser Ser Ser Thr Ala Arg Gly Asp Val Trp Glu Ser Thr Leu
            100                 105                 110

Val Gly Cys Asp Ser Phe Thr Lys Thr Ala Pro Thr Glu Gln Gln Ile
        115                 120                 125

Ala His Ala Gln Leu His Cys Arg Ala Pro Arg Leu Lys
    130                 135                 140
```

<210> SEQ ID NO 5
<211> LENGTH: 25
<212> TYPE: DNA
<213> ORGANISM: Artificial Sequence
<220> FEATURE:
<223> OTHER INFORMATION: Synthetic primer Tm2NtermPci

<400> SEQUENCE: 5
aaaacatgtc agacgttcaa tcttc       25

<210> SEQ ID NO 6
<211> LENGTH: 28
<212> TYPE: DNA
<213> ORGANISM: Artificial Sequence
<220> FEATURE:
<223> OTHER INFORMATION: Synthetic primer Tm2CtermBam

<400> SEQUENCE: 6
tttggatcct tacttcaacc tcggtgcg       28

<210> SEQ ID NO 7
<211> LENGTH: 21

```
<212> TYPE: DNA
<213> ORGANISM: Artificial Sequence
<220> FEATURE:
<223> OTHER INFORMATION: Synthetic forward primer for PCR Tm2 N115C

<400> SEQUENCE: 7
cttgtggggt gtgattcgtt t                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic reverse primer for PCR Tm2 N115C

<400> SEQUENCE: 8
aaacgaatca caccccacaa g                                              21
```